(12) United States Patent
Harder et al.

(10) Patent No.: US 8,501,775 B2
(45) Date of Patent: Aug. 6, 2013

(54) ANTHELMINTICS FOR PREVENTING PARASITIC INFECTIONS IN HUMANS AND ANIMALS

(75) Inventors: Achim Harder, Cologne (DE); Georg von Samson-Himmlstjerna, Mellendorf (DE); Bernd-Wieland Kruger, Gladbach (DE); Heinz Melhorn, Neuss (DE); Jurgen Schmidt, Dusseldorf (DE)

(73) Assignee: SALTIGO GmbH, Langenfeld (DE)

( * ) Notice: Subject to any disclaimer, the term of this patent is extended or adjusted under 35 U.S.C. 154(b) by 1443 days.

(21) Appl. No.: 12/117,939

(22) Filed: May 9, 2008

(65) Prior Publication Data

US 2013/0172385 A1   Jul. 4, 2013

Related U.S. Application Data

(63) Continuation of application No. 10/311,418, filed as application No. PCT/EP01/07201 on Jun. 25, 2001, now abandoned.

(30) Foreign Application Priority Data

Jul. 6, 2000  (DE) .................................. 100 32 878

(51) Int. Cl.
*A01N 43/40*  (2006.01)
*A61K 31/445*  (2006.01)
*C07D 211/60*  (2006.01)

(52) U.S. Cl.
USPC ........................................... 514/315; 546/245

(58) Field of Classification Search
USPC ........................................... 514/315; 546/245
See application file for complete search history.

(56) References Cited

U.S. PATENT DOCUMENTS

| | | |
|---|---|---|
| 4,810,489 A | 3/1989 | Murray et al. |
| 4,900,834 A | 2/1990 | Kruger et al. |
| 5,518,712 A | 5/1996 | Stewart et al. |
| 5,716,602 A | 2/1998 | Uick |
| 6,147,091 A * | 11/2000 | Kruger et al. ................. 514/315 |

OTHER PUBLICATIONS

Salafsky et al. "Evaluation of N,N-diethyl-m-toluamide (DEET) as a topical agent for preventing skin penetration by cercariae of *Schistosoma mansoni*" Am. J. Trop. Med. Hyg., 1998, vol. 58, No. 6, pp. 828-834.*
Weinmann et al. "Filarial Worms of Columbian Black-Tailed Deer in California" Journal of Wildlife Diseases, 1973, vol. 9, pp. 213-220.*
Boeckh et al. "Acylated 1,3-Aminopropanols as Repellents against Bloodsucking Arthropods" Pestic. Sci, 1996, vol. 48, pp. 359-373.*

* cited by examiner

*Primary Examiner* — Kendra D Carter
(74) *Attorney, Agent, or Firm* — Michael A. Miller

(57) ABSTRACT

The present invention relates to compositions comprising certain active compounds which are suitable as repellents, and to their use for preventing an infection of humans or of animals by the infectious states of parasitic flatworms (platyhelminths).

3 Claims, No Drawings

ANTHELMINTICS FOR PREVENTING PARASITIC INFECTIONS IN HUMANS AND ANIMALS

This application is a continuation of U.S. patent application Ser. No. 10/311,418 filed Jun. 12, 2003, incorporated herein by reference.

The present invention relates to compositions comprising certain active compounds which are suitable as repellents, and to their use for preventing an infection of humans or of animals by the infectious stages of parasitic flatworms (platyhelminths). The compositions are used on the skin against the flatworm stages which are capable of penetrating through the skin into the host organism (cercariae).

Several platyhelminth species cause serious diseases in humans and animals. In tropical countries, infections with *Schistosoma* species in particular cause chronic suffering and frequently death. Important pathogens are *Schistosoma mansoni*, *Schistosoma haematobium* and *Schistosoma japonicum*. Affected are the local population, tourists, people working for humanitarian aid organizations and military personnel. In the case of infections of humans, the infectious cercariae, which are present in the water of open bodies of water penetrate through the skin into the body.

Likewise problematic, in countries with a moderate climate, is the infection of humans by cercariae of various species of the genera *Trichobilharzia* and *Ornithobilharzia*, which can drill into the skin, causing dermatitis. Such infections occur during leisure activities on inland waters or sea coasts and during fishing, working on ponds or watering fields. In general, in many situations of daily life, contact of the skin with possibly contaminated/infected water is unavoidable.

Protection against penetration of the pathogens is, however, possible by pretreating the skin according to the invention with anthelmintic substances.

In the past, some compounds have already been tested for their suitability for preventing infections with such parasites. However, the substances hitherto described for the purposes according to the invention are toxic if they get into the body either through the skin or orally:

Thus, for example, hexachlorophene has a lethal effect on cercariae of *Schistosoma mansoni* (Fripp, P. J. and Armstrong, F. I., The efficacy of hexachlorophene skin cleanser as a cercariae repellent. South African Med. J. 47: 1973, 526-527). Because of health risks, in particular liver damage, hexachlorophene cannot be used on the skin of humans. It is toxic on contact with the skin and when swallowed, may possibly cause deformities and is possibly carcinogenic [Commission of the European Community, Directive 93/72/EEC of 1 Sep. 1993, Annex Vol. 1 and II (EU Directive on Dangerous Substances) with amendments to 1999, Official Journal EUL258A, Volume 36, 16 Oct. 1993, Amendments to 1997].

Niclosamide acts against the penetration of cercariae [Bruce, J. I. et al. (1992) Efficacy of niclosamide as a potential topical antipenetrant (TAP) against cercariae of *Schistosoma mansoni* in monkeys. Mem. Inst. Oswaldo Cruz 87:28, I-289.] but is toxicologically objectionable since it may possibly cause inheritable genetic damage (Registry of Toxic Effects of Chemical Substances, National Institute of Occupational Safety and Health). Use on the skin in cases where the user is exposed to water has to be ruled out owing to the risk it poses to the environment, since niclosamide constitutes a water hazard [Federal Office for the Environment (Ed.), Catalogue of substances hazardous to water. LTwS No. 12 May 1996 with current amendments, Berlin 1996]. Accordingly, the compound has hitherto been used commercially in humans against cercariae.

N,N-Diethyl-m-toluamide (DEFT) acts against cercariae of *Schistosoma mansoni* [Salafsky, B. et al. Evaluation of N,N-diethyl-m-toluamide (DEET) as a topical agent for preventing skin penetration by cercariae of *Schistosoma mansoni*. Am. J. Trop. Med. Hyg. 58: 1998, 828-834). However, DEET has some unfavourable properties.

The effect of the anthelmintics hitherto described against infections states of platyhelminths has hitherto only been tested on cercariae of the species *Schistosoma mansoni*. i.e. an efficacy of these agents against other worm species had hitherto not been demonstrated.

Surprisingly, it has now been found that the compositions according to the invention are suitable for protecting humans and animals effectively against infections by platyhelminths, in particular *Schistosoma haematobium*, *Schistosoma japonicum*, *Trichobilharzia* spp. and *Ornithobilharzia* spp., but also *Echinostoma* spp. and others.

Accordingly, the invention relates to

1. Compositions for deterring helmintic parasites, characterized in that they comprise at least one compound of the formula (I)

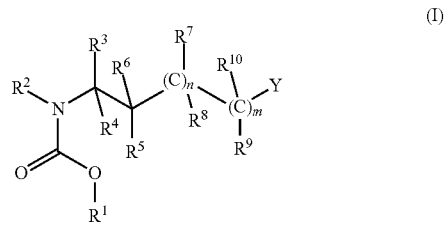

in which
represents hydrogen, optionally substituted alkyl or the radical O—X,
X represents hydrogen, $COR^{11}$, $COOR^{12}$ or $R^{13}$,
$R^1$ represents an optionally substituted alkyl, alkenyl, alkynyl, cycloalkyl or cycloalkenyl radical,
$R^2$, $R^{11}$, $R^{12}$ and $R^{13}$ are identical or different and represent optionally substituted alkyl or alkenyl radicals,
$R^3$ and $R^{10}$ are identical or different and represent hydrogen or represent optionally substituted alkyl radicals, where $R^2$ and $R^3$ or $R^3$ and $R^7$ or $R^3$ and $R^5$ or $R^5$ and $R^7$ together with the atoms to which they are attached may also form an optionally substituted monocyclic ring
and
n and m are identical or different and are 0 or 1.

2. Compositions for deterring helmintic parasites according to item 1, characterized in that they comprise at least one compound of the formula (I)
in which
Y represents hydrogen, $C^1$-$C^6$-alkyl or the radical O—X,
X represents hydrogen, $COR^{11}$ or $R^{13}$,
$R^1$ represents $C^3$-$C^7$-cycloalkyl, $C^3$-$C^7$-cycloalkenyl, $C^1$-$C^2$-alkyl-$C^3$-$C^7$-cycloalkyl, $C^1$-$C^2$-alkyl-$C^3$-$C^7$-cycloalkenyl, where the cycloalkyl or cycloalkenyl rings of the abovementioned radicals are optionally substituted up to three times by $C^1$-$C^6$-alkyl or by a $C^1$-$C^6$-dialkylene bridge, or
$R^1$ represents $C_1$-$C_7$-alkyl, $C_2$-$C_7$-alkenyl or $C_2$-$C_7$-alkynyl,
$R^2$, $R^{11}$, $R^{13}$ are identical or different and represent $C_1$-$C_6$-alkyl, $R^3$ to $R^8$ are identical or different and represent hydrogen or $C_1$-$C_6$-alkyl, where $R^2$ and $R^3$ or $R^3$ and $R^7$ or $R^3$ and $R^5$ or $R^5$ and $R^7$ together with the atoms to which they are attached may also form a 5- or 6-membered monocyclic ring and n represents 1 and m represents 0.

3. A method for deterring helmintic parasites, characterized in that compounds of the formula (I) according to item 1 are applied to the skin of the organism to be protected.
4. The use of compounds of the formula (I) according to item 1 for deterring helmintic parasites.
5. A process for preparing compositions for deterring helminthic parasites, characterized in that compounds of the formula (I) according to Claim 1 are mixed with extenders and/or surfactants.

In a preferred embodiment, the substituent Y in the formula (I) represents hydrogen or $C_1$-$C_6$-alkyl, such as, for example, methyl, ethyl, propyl, isopropyl, n-butyl, sec-butyl, iso-butyl or tert-butyl, pentyl or hexyl. In this case, $R^1$ preferably represents $C_3$-$C_7$-cycloalkyl, $C_3$-$C_7$-cycloalkenyl, $C_1$-$C_2$-alkyl-$C_3$-$C_7$-cycloalkenyl, where the cycloalkyl or cycloalkenyl rings of the abovementioned radicals are optionally substituted up to three times by $C_1$-$C_6$-alkyl or by a $C_1$-$C_6$-dialkylene bridge.

According to a further embodiment, the compounds of the formula (I) used in the compositions according to the invention are compounds in which Y represents the radical O—X,
X represents hydrogen, $COR^{11}$, $COOR^{12}$ or $R^{13}$
$R^1$ represents optionally substituted alkyl, cycloalkyl, alkenyl or alkynyl radicals,
$R^2$, $R^{11}$, $R^{12}$ and $R^{13}$ are identical different and represent optionally substituted alkyl or alkenyl radicals,
$R^3$ to $R^{10}$ are identical or different and represent hydrogen or represent optionally substituted alkyl radicals, where $R^2$ and $R^3$ or $R^3$ and $R^7$ or $R^3$ and $R^5$ or $R^5$ and $R^7$ together with the atoms to which they are attached may also form an optionally substituted monocyclic ring and
n and m are identical or different and are 0 or 1.

Among these, preference is given to the compounds of the formula (I) in which
X represents hydrogen, $COR^{11}$ or $R^{13}$,
$R^1$ represents $C_1$-$C_7$-alkyl, $C_3$-$C_7$-cycloalkyl, $C_2$-$C_7$-alkenyl or $C_2$-$C_7$-alkynyl,
$R^2$, $R^{11}$, $R^{13}$ are identical or different and represent $C_1$-$C_6$-alkyl,
$R^3$-$R^8$ are identical or different and represent hydrogen or $C_1$-$C_6$-alkyl, where $R^2$ and $R^3$ or $R^3$ and $R^7$ or $R^3$ and $R^5$ and $R^7$ together with the atoms to which they are attached may also form a 5- or 6-membered monocyclic ring and
n represents 1 and m represents 0.

Among these, particular reference is given to compounds of the formula (I)
in which
X represents hydrogen or $R^{13}$,
where $R^{13}$ represents $C_1$-$C_6$-alkyl,
$R^1$ represents $C_1$-$C_7$-alkyl or $C_3$-$C_7$-alkenyl,
$R^4$ to $R^8$ are identical or different and represent hydrogen or $C_1$-$C_6$-alkyl,
$R^2$ and $R^3$ together with the atoms to which they are attached from a 5- or 6-membered monocyclic ring,
n represents 1 and
m represents 0.

Furthermore, from among the compounds in which Y represents the radical O—X, preference is given to those compounds in which $R^1$ represents $C_1$-$C_7$-alkyl, $C_3$-$C_7$-cycloalkyl or $C_3$-$C_7$ alkenyl, X represents $COR^{11}$ or $R^{13}$, $R^2$ and $R^{11}$ are identical or different and represent $C_1$-$C_6$-alkyl. $R^3$ to $R^8$ are identical or different and represent hydrogen or $C_1$-$C_6$-alkyl, $R^{13}$ represents $C_1$-$C_6$-alkyl and n represents 1 and m represents 0.

Very particularly preferred for use in the compositions according to the invention are compounds of the general formula (I) in which
Y represents the radical O—X,
m=0 and n=1,
$R^1$ represents $C_1$-$C_4$-alkyl or $C_5$-$C_6$-cycloalkyl,
$R^2$, $R^{11}$ and $R^{13}$ are identical or different and represent $C_1$-$C_6$-alkyl, $R^3$ to $R^8$ represent hydrogen and X represents hydrogen, $COR^{11}$ or $R^{13}$, where $R^{11}$ and $R^{13}$ are as defined above.

Furthermore, very particularly preferred for use in the compositions according to the invention are compounds of the general formula (I) in which m=0 and n=1, R1 represents $C_1$-$C_4$-alkyl, $R^2$ and $R^3$ together with the atoms to which they are attached form a 6-membered piperazine ring, $R^4$ to $R^8$ represent hydrogen and X represents hydrogen or $R^{13}$, where $R^{13}$ represents $C_1$-$C_4$-alkyl.

Examples which may be mentioned of compounds in which $R^2$ and $R^3$ together with the atoms to which they are attached form an optionally substituted monocyclic ring are the following:

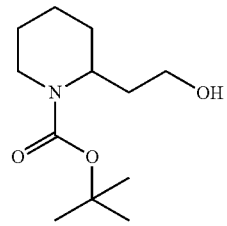 [SMILES: CC(C)(C)OC(=O)N1CCCCC1CCO]
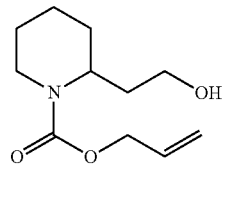
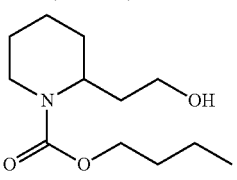 [SMILES: CCCCOC(=O)N1CCCCC1CCO]
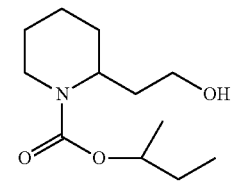 [SMILES: CCC(C)OC(=O)N1CCCCC1CCO]

Examples which may be mentioned of compounds in which R2 and R3 do not form a ring are the following:

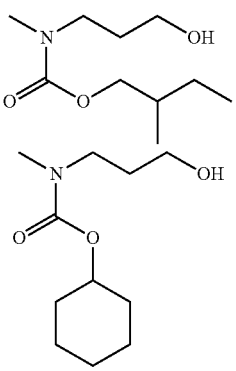
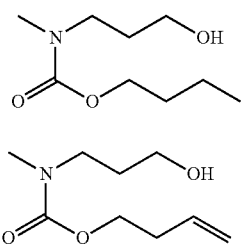

The compounds of the general formula (I) are either known, or they can be prepared by generally known methods and processes (cf., for example, Cesare Ferri, Reaktionen der organischen Synthese [Reactions of Organic Synthesis], Georg Thieme Verlag Stuttgart, 1978, p. 223 and p. 450, and also EP A 0 289 842).

The active compounds contained in the compositions according to the invention have already been used specifically as repellents on the skin, against insects and ticks.

A substantial advantage of using the compounds according to the invention is their high compatibility with the skin, plants and the environment and the generally low toxicity of these compounds.

When staying outdoors, it is furthermore desirable to be protected against mosquitoes which, on the one hand, are considered a nuisance and, on the other hand, specifically in tropical regions, may transfer diseases such as malaria, various viruses, filarial and parasites by means of their sting. The compositions according to the invention now allow simultaneous prevention of platyhelminth infection and protection against mosquitoes, with only one composition. Thus, the necessity for using simultaneously two different, possibly incompatible compositions on the skin is avoided.

In addition to the active compounds, the compositions according to the invention may also comprise all of the customary auxiliaries and additives used in formulations for topical application.

The active compounds are administered, either directly or in the form of suitable preparations, dermally or with the aid of shaped articles containing the active compound, such as, for example, strips, plates, tapes, collars, ear tags, limb bands or marking devices.

Dermal administration is effected, for example, in the form of bathing, dipping, spraying, pouring-on or spotting-on, washing, shampooing, or powdering.

Suitable preparations include:
solutions or concentrates for administration after dilution, solutions for use on the skin, pour-on formulations, gels;
emulsions and suspensions for dermal administration and also semisolid preparations;
formulations in which the active compound is incorporated in an ointment base or in an oil-in-water or water-in-oil emulsion base;
solid preparations, such as powders, shaped articles containing the active compound.

Solutions for use on the skin are applied drop by drop, brushed on, rubbed in, splashed on or sprayed on, or applied by dipping, bathing or washing.

The solutions are prepared by dissolving the active compound in a suitable solvent and adding, if appropriate, additives such as solubilizers, acids, bases, buffer salts, antioxidants, preservatives.

Suitable solvents include: physiologically acceptable solvents, such as water, alcohols, such as ethanol, butanol, benzyl alcohol, glycerol, hydrocarbons, propylene glycol, polyethylene glycols and N-methyl-pyrrolidone, and their mixtures.

If appropriate, the active compounds can also be dissolved in physiologically acceptable vegetable or synthetic oils.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

Suitable preservatives are: benzyl alcohol, trichlorobutanal, p-hydroxybenzoic esters or n-butanol.

It may be advantageous to add thickeners when preparing the solutions. Suitable thickeners are: inorganic thickeners, such as bentonites, colloidal silica, aluminum monostearate, or organic thickeners, such as cellulose derivatives, polyvinyl alcohols and their copolymers, acrylates and methacrylates.

Gels which are applied to the skin or smoothed on are prepared by adding such an amount of thickener to solutions which have been prepared as described above that a clear composition is formed which has an ointment-like consistency. The thickeners used are the thickeners indicated further above.

Pour-on and spot-on formulations are poured or splashed onto limited areas of the skin, the active compound distributing itself over the surface of the body.

Pour-on and spot-on formulations are prepared by dissolving, suspending or emulsifying the active compound in suitable skin-compatible solvents or solvent mixtures. If appropriate, other auxiliaries, such as colorants, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol, phenoxyethanol, esters, such as ethyl acetate, butyl acetate, benzyl benzoate, ethers, such as alkylene glycol alkyl ethers, such as dipropylene glycol monomethyl ether, diethylene glycol monobutyl either, ketones, such as acetone, methyl ethyl ketone, aromatic and/or aliphatic hydrocarbons, vegetable or synthetic oils, DMF, dimethylacetamide, N-methylpyrrolidone, 2-dimethyl-4-oxy-methylene-1,3-dioxolane.

Colorants are all colorants which can be dissolved or suspended and which are approved for use in animals.

Auxiliaries include spreading oils, such as isopropyl myristate, dipropylene glycol pelargonate, silicone oils, fatty acid esters, triglycerides or fatty alcohols.

Antioxidants are sulphites or metabisulphites, such as potassium metabisulphite, ascorbic acid, butylhydroxytoluene, butylhydroxyanisole, tocopherol.

Examples of photostabilizers are substances from the class of the benzophenones and novantisolic acid.

Tackifiers are, for example, cellulose derivatives, starch derivatives, polyacrylates, natural polymers such as alginates, gelatin.

Emulsions are either of the water-in-oil or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, bioabsorption promoters, preservatives, antioxidants, photostabilizers, and viscosity-increasing substances.

Suitable hydrophobic phases (oils) include: paraffin oils, silicone oils, natural vegetable oils, such as sesame seed oil, almond oil, castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, mono- and diglycerides of the $C_8/C_{10}$-fatty acids.

Fatty acid esters, such as ethyl, stearate, di-n-butyryl adipate, hexyl laurate, dipropylene glycol pelargonate, esters of a branched fatty acid having a medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, amongst other fatty alcohols, such as isotridecyl alcohol, 2-otyldodecanol, cetyl-stearyl alcohol or oleyl alcohol.

Fatty acids, such as, for example oleic acid and its mixtures.

Suitable hydrophilic phases include:
water, alcohols, such as, for example, propylene glycol, glycerol, sorbitol and their mixtures.

Suitable emulsifiers include: nonionic surfactants, for example polyethoxylated castor oil, polyethoxylated sorbitan monooleate, sorbitan monostearate, glycerol monostearate, polyethoxy stearate, alkylphenol polyglycol ethers;
ampholytic surfactants, such as disodium N-lauryl-β-iminodipropionate or lecithin;
anionic surfactants, such as sodium lauryl sulphate, fatty alcohol ether sulphates, and the monoethanolamine salt of mono/dialkylpolyglycol ether orthophosphoric ester;
cationic surfactants, such as cetyltrimethylammonium chloride.

Other suitable auxiliaries include: substances which increase the viscosity and stabilize the emulsion, such as carboxymethylcellulose, methylcellulose and other cellulose and starch derivatives, polyacrylates, alginates, gelatin, gum Arabic, polyvinylpyrrolidone, polyvinyl alcohol, methylvinyl ether/maleic anhydride copolymers, polyethylene glycols, waxes, colloidal silica, or mixtures of the listed substances.

Suspensions are prepared by suspending the active compound in a liquid excipient, if appropriate with the addition of other auxiliaries, such as wetting agents, colorants, bioabsorption promoters, preservatives, antioxidants and photostabilizers.

Suitable liquid excipients include all homogeneous solvents and solvent mixtures.

Suitable wetting agents (dispersants) include the surfactants indicated further above.

Other suitable auxiliaries include those indicated further above.

Semi-solid preparations for dermal administration differ from the suspensions and emulsions described above only in that they have a higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, sodium chloride, carbonates, such as calcium carbonate, hydrogen carbonates, aluminium oxides, silicas, clays, precipitated or colloidal silica, and phosphates.

Auxiliaries are preservatives, antioxidants and colorants which have already been mentioned further above.

Other suitable auxiliaries are lubricants and glidants, such as, for example, magnesium stearate, stearic acid, talc, bentonites.

It is furthermore desirable for such a protective agent to have a sufficient protective action even after prolonged contact with water, for example when swimming, washing clothes or fishing. To this end, the compositions according to the invention may additionally comprise water-repelling or water-proof substances.

Suitable water-proof substances are already being used in sun protection compositions which are to protect the user against the UV radiation from the sun (for example U.S. Pat. No. 5,518,712 and U.S. Pat. No. 4,810,489). Here, it is intended to maintain sun protection even after the user has been swimming, is sweating heavily, etc. Sun protection compositions which comprise such water-proof or water-repelling substances and insect repellents are already known (U.S. Pat. No. 5,716,602). However, compositions which comprise anthelmintics have hitherto not been described.

Accordingly, water-proof substances may also be present in the composition according to the invention. These may be substances which are soluble in fat and insoluble in water, and compounds which improve adherence of the composition to the skin.

Skin protection products may comprise, as water-proof components, for example from 1 to 50% by weight of a polymer such as polyvinylpyrrolidones, polyacrylates, silicones, etc.

The compositions for topical application can be formulated as sprays, solutions, creams, ointments or layer- or film-forming compositions, according to the known processes for manufacturing cosmetics (Schrader, K. (1979) Grundlagen and Rezepturen der Kosmetika [Principles of and recipes for cosmetics], Dr. Alfred Hüthig Verlag, Heidelberg).

For use, the formulations according to the invention are applied evenly and without any gaps onto the skin, in amounts appropriate for the user.

The compositions according to the invention are of course also suitable for use on animals to prevent infection of the animals with parasites of these genera. The compositions can be used for pets, such as, for example, dogs and cats, and for economically useful animals, for example cattle, pigs, sheep, etc.

When using the compositions according to the invention, in general from 0.03 to 1 mg, preferably from 0.03 to 0.1 mg and particularly preferably from 0.04 to 0.06 mg of the active compound are applied per $cm^2$ of skin. This results in prophylactic protection against skin-penetrating worms and juvenile stages thereof. If the user stays in the water for a longer time, the active compound has to be applied repeatedly.

The examples below illustrate the compositions according to the invention, but without limiting them.

BIOLOGICAL EXAMPLE

Activity Against *Schistosoma mansoni* Cercariae
[500 µl/l final concentration of the active compounds]

Snails (*Biomphalaria glabrata*) were infected by incubating each of them with 8 miracidia in 10 ml of water overnight. About 6 to 9 weeks after the infection, cercariae were obtained by irradiating the snails, which had been kept in darkness, with light, followed by collection of the swarming cercariae within 2 hours.

Such an amount of cercariae-containing water (1 or 2 ml, see below) was added to the test batches that each batch contained about 100 to 150 cercariae.

5 µl of active compound were mixed thoroughly with 25 µl of PEG300. 9 ml of aquarium water was then added, and the batch was shaken vigorously. After (delayed) addition of 1 ml of cercariae suspension, survival of the cercariae was in each case observed immediately using a stereomagnifier. The activity of the active compounds was assessed using the following classification: 0=no effect during the entire test period of 120 minutes; 1=weak effect (the cercariae have a strongly reduced mobility); 2=good effect (the cercariae are only slightly mobile and bent); 3=full effect (the cercariae are completely immobile).

Assessment of different compounds according to the invention:

| Compound | Assessment |
|---|---|
| (2-(2-hydroxyethyl)piperidine-1-carboxylic acid tert-butyl ester) | 3 |
| (2-(2-hydroxyethyl)piperidine-1-carboxylic acid allyl ester) | 3 |
| (2-(2-hydroxyethyl)piperidine-1-carboxylic acid butyl ester) | 3 |
| (2-(2-hydroxyethyl)piperidine-1-carboxylic acid sec-butyl ester) | 2 |
| (methyl(3-hydroxypropyl)carbamic acid 2-methylbutyl ester) | 1 |
| (methyl(3-hydroxypropyl)carbamic acid butyl ester) | 1 |
| (methyl(3-hydroxypropyl)carbamic acid cyclohexyl ester) | 1 |

| Compound | Assessment |
|---|---|
| (methyl(3-hydroxypropyl)carbamic acid 3-butenyl ester) | 2 |

The invention claimed is:

1. A method for deterring helmintic parasites comprising applying a compound of formula (I)

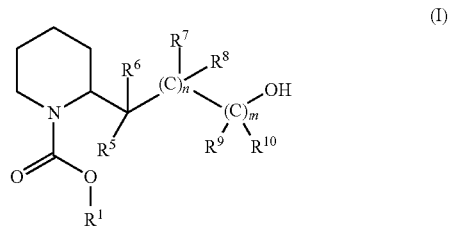

(I)

in which

R$^1$ represents an optionally substituted alkyl, alkenyl, alkynyl, cycloalkyl or cycloalkenyl radical, R$^5$ to R$^{10}$ are identical or different and represent hydrogen or represent optionally substituted alkyl radicals, and n and m are identical or different and are 0 or 1, to the skin of the organism to be protected in an effective amount to deter helmintic parasites.

2. The method according to claim 1, wherein the compound of formula (I) is a compound with the following formula

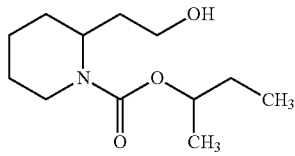

3. The method according to claim 1, wherein the effective amount is 0.03 to 1 mg of compounds according to formula (I) per cm$^2$ of skin.

* * * * *